United States Patent [19]

Alderman et al.

[11] Patent Number: 4,853,219

[45] Date of Patent: Aug. 1, 1989

[54] ANTIBODIES TO ANGIOGENIN: IMMUNOTHERAPEUTIC AGENTS

[75] Inventors: Edward M. Alderman, Dedham; James W. Fett, Waltham; Bert L. Vallee, Brookline, all of Mass.

[73] Assignee: President and Fellows of Harvard College, Cambridge, Mass.

[21] Appl. No.: 83,231

[22] Filed: Aug. 6, 1987

[51] Int. Cl.[4] .................... A61K 39/395; C07K 15/16
[52] U.S. Cl. .................... 424/85.8; 530/387; 530/395; 530/808; 530/809; 530/828; 530/399; 435/240.27; 935/104
[58] Field of Search .................... 530/387, 806, 828; 424/85, 88; 435/68, 240.26; 935/104, 95

[56] References Cited

U.S. PATENT DOCUMENTS

| | | | |
|---|---|---|---|
| 4,229,532 | 10/1980 | Tolbert et al. | 424/95 |
| 4,273,871 | 6/1981 | Tolbert et al. | 435/240.23 |
| 4,503,038 | 3/1985 | Banda et al. | 424/95 |
| 4,529,590 | 1/1985 | Leveen . | |
| 4,698,301 | 10/1987 | Weiss et al. | 424/95 |
| 4,699,788 | 10/1987 | Catsimpoolas et al. | 424/104 |
| 4,727,137 | 2/1988 | Vallee et al. | 530/412 |

FOREIGN PATENT DOCUMENTS 0234545 9/1987 European Pat. Off. .
8616079 10/1986 World Int. Prop. O. .

OTHER PUBLICATIONS

Lancet 1, 682, Mar. 1980, Brown et al.
Fett et al., Biochemistry, vol. 24, pp. 5480–5486 (1985).
Shapiro et al., Biochemistry, 26(16), 5141–5146, 1987 (mid-August).
Osthoff et al., Bioch. Biophys. Res. Comm., 146(3), (Aug. 1987) pp. 945–952.

*Primary Examiner*—Margaret Moskowitz
*Assistant Examiner*—Jeff P. Kushan
*Attorney, Agent, or Firm*—Allegretti & Witcoff, Ltd.

[57] ABSTRACT

This invention relates to the production of antibodies to angiogenin or to fragments thereof and to methods of inhibiting angiogenesis in mammals by administering to mammals such antibodies or Fab fragments thereof so as to inhibit angiogenic activity. In addition, this invention relates to pharmaceutical compositions comprising therapeutically effective amounts of antibody that are immunologically reactive with angiogenin and which can be administered to inhibit angiogenesis.

1 Claim, No Drawings

ANTIBODIES TO ANGIOGENIN: IMMUNOTHERAPEUTIC AGENTS

BACKGROUND OF THE INVENTION

1. Field of the Invention

Angiogenesis is the process of increased vascularization in response to an angiogenic factor. It occurs as a result of the endothelial cells in the existing blood vessels being stimulated into mitosis, thereby producing a new capillary network which advances towards its stimulus.

Solid tumors in situ are supported by an extensive vascular network which supplies the tumor with nutrients and eliminates its waste. This extensive vascular network is thought to develop from the host's normal and less extensive vascular network in response to the secretion of substances known as tumor angiogenic factor.

Angiogenic factors are not specific for tumors alone. Recently, an angiogenic factor has been isolated from the joint fluid of patients suffering from the inflammatory disease, rheumatoid arthritis. This angiogenic factor was isolated from the synovial fluid of the inflamed joint and was serologically identical with the tumor angiogenic factor isolated from animals with experimental cancers. (Lancet 1, 682, Mar. 1980).

In addition, angiogenesis is associated with the pathological condition known as diabetic retinopathy and also with normal wound healing.

The present invention relates to antibodies specific for the human angiogenic factor, angiogenin. The antibodies of the present invention bind to the human angiogenin molecule inhibiting its activity, thereby inhibiting angiogenesis. The antibodies of the present invention are useful agents for inhibiting angiogenisis in humans and other mammals such as in the treatment of tumors, diabetic retinopathy, inflammatory diseases, and disease states where angiogenesis is not desired.

2 Description of the Related Art

LeVeen, U.S. Pat. No. 4,529,590, describes a method for producing a bovine angiogenic factor. LeVeen's method consists of inducing a prolonged inflammatory response in the cattle secondary to the injection of irritants into the body cavity of the animal. The angiogenic material which LeVeen isolated from fluid at the sits of irritation was only partially characterized; it tested positive for angiogenic activity on chick chorioallantoic membrane and was capable of evoking an immune response in animals.

Vallee et al. U.S. patent application Ser. No. 778,387 filed Sept. 20, 1985, hereby incorporated by reference described purification and characterization of angiogenin, an angiogenic protein from human adenocarcinoma cell line HT-29. Angiogenin was also described in Fett et al., Biochemistry, Vol. 24, pp. 5480–5486 (1985).

The present invention relates to antibodies specific to human angiogenin, and to therapeutic compositions containing them as well as their use in inhibiting angiogenesis in mammals.

SUMMARY OF THE INVENTION

This invention relates to the production of monoclonal and polyclonal antibodies (herein referred to as antibody) immunologically reactive with angiogenin, in particular, angiogenin having the amino acid sequence in Formula 1 below. The antibodies can be raised by challenging mammals, e.g. mice or rabbits, either with angiogenin or with various fragments of angiogenin, prepared either by synthesis or by degradation of angiogenin itself. The fragments of angiogenin used each contains one or more epitopes, functional subunits, or active sites. Antibodies raised to such fragments may display less undesirable cross-reactivity with foreign proteins than do antibodies raised to whole angiogenin; consequently, antibodies to fragments of angiogenin may produce fewer undesirable side effects when used therapeutically than do antibodies to whole angiogenin. The antibodies raised to such fragments of angiogenin are immunologically reactive to whole angiogenin.

Formula I is as follows:

$$\begin{aligned}
&1\\
&<\text{Glu}-\text{Asp}-\text{Asn}-\text{Ser}-\text{Arg}-\text{Tyr}-\text{Thr}-\text{His}-\text{Phe}-\text{Leu}-\\
&\phantom{<\text{Glu}}15\\
&-\text{Thr}-\text{Gln}-\text{His}-\text{Tyr}-\text{Asp}-\text{Ala}-\text{Lys}-\text{Pro}-\text{Gln}-\text{Gly}-\\
&\phantom{<\text{Glu}}30\\
&-\text{Arg}-\text{Asp}-\text{Asp}-\text{Arg}-\text{Tyr}-\text{Cys}-\text{Glu}-\text{Ser}-\text{Ile}-\text{Met}-\\
&-\text{Arg}-\text{Arg}-\text{Arg}-\text{Gly}-\text{Leu}-\text{Thr}-\text{Ser}-\text{Pro}-\text{Cys}-\text{Lys}-\\
&\phantom{<\text{Glu}}45\\
&-\text{Asp}-\text{Ile}-\text{Asn}-\text{Thr}-\text{Phe}-\text{Ile}-\text{His}-\text{Gly}-\text{Asn}-\text{Lys}-\\
&\phantom{<\text{Glu}}60\\
&-\text{Arg}-\text{Ser}-\text{Ile}-\text{Lys}-\text{Ala}-\text{Ile}-\text{Cys}-\text{Glu}-\text{Asn}-\text{Lys}-\\
&-\text{Asn}-\text{Gly}-\text{Asn}-\text{Pro}-\text{His}-\text{Arg}-\text{Glu}-\text{Asn}-\text{Leu}-\text{Arg}-\\
&\phantom{<\text{Glu}}75\\
&-\text{Ile}-\text{Ser}-\text{Lys}-\text{Ser}-\text{Ser}-\text{Phe}-\text{Gln}-\text{Val}-\text{Thr}-\text{Thr}-\\
&\phantom{<\text{Glu}}90\\
&-\text{Cys}-\text{Lys}-\text{Leu}-\text{His}-\text{Gly}-\text{Gly}-\text{Ser}-\text{Pro}-\text{Trp}-\text{Pro}-\\
&-\text{Pro}-\text{Cys}-\text{Gln}-\text{Tyr}-\text{Arg}-\text{Ala}-\text{Thr}-\text{Ala}-\text{Gly}-\text{Phe}-\\
&\phantom{<\text{Glu}}105\\
&-\text{Arg}-\text{Asn}-\text{Val}-\text{Val}-\text{Val}-\text{Ala}-\text{Cys}-\text{Glu}-\text{Asn}-\text{Gly}-\\
&\phantom{<\text{Glu}}120\\
&-\text{Leu}-\text{Pro}-\text{Val}-\text{His}-\text{Leu}-\text{Asp}-\text{Gln}-\text{Ser}-\text{Ile}-\text{Phe}-\\
&\phantom{<\text{Glu}}123\\
&\phantom{<\text{Glu}-\text{Asp}-\text{Asn}-\text{Ser}-\text{Arg}-\text{Tyr}}-\text{Arg}-\text{Arg}-\text{Pro}-\text{OH}.
\end{aligned}$$

DETAILED DESCRIPTION

A. Production of Polyclonal Antibodies:

(a) Immunization: Antibodies to human tumor angiogenin or fragments thereof are produced in both rabbits and mice by injection with the appropriate immunogen preparation. Rabbits are immunized by subcutaneous injections with a suspension comprising purified angiogenin conjugated to affinity gel beads which are emulsified in 1 ml of complete or incomplete Freund's adjuvant just prior to use. Alternatively, the rabbits are injected subcutaneously with purified angiogenin and/or synthetic peptide derivatives conjugated to keyhole Limpet hemocyanin which is likewise emulsified in 1 ml of complete or incomplete Freund's adjuvant immediately prior to injection.

Similarly, the mice are immunized by injection with purified angiogenin or fragments thereof conjugated to affinity gel beads which are emulsified in complete Freund's adjuvant just prior to injection. However, unlike the rabbits, the mice are preferably injected with the immunogen in the peritoneal cavity.

(b) Purification of Polyclonal Antibodies:

Pursuant to immunization at ten day intervals, sera is collected from both rabbits and mice five days following each injection and assayed for the presence of specific antibody by ELISA (enzyme linked immunosorbant assay). Once antibodies to angiogenin are detected, the antibodies present in the sera are purified in a multistep process consisting of precipitation by saturated ammonium sulfate, resuspension in saline, dialysis against normal saline, affinity gel chromatography on Protein A-Sepharose, further dialysis against water, and then lyophilization.

The resultant purified antibody preparations contain polyclonal antibodies raised to angiogenin or fragments thereof which are utilized in the therapeutic studies later described.

B. Production of Monoclonal Antibodies:

(a) Fusion: A Balb/c mouse is immunized with a total of 100 ng of purified angiogenin, and the splenocytes from this mouse are mixed, and copelleted with the cells from the plasmacytoma line HMS 3.3, a subline of P3x63Ag8.653; CRL 1580. Fusion so as to form a hybridoma cell occurs upon the addition of polyethylene glycol (400–600 cp) to the copelleted cells. The resulting cell pellet is resuspended in a supplemented RPMI-1640 medium. The resuspended cells are then plated to tissue plates (100 $\mu$l/well) and incubated at 37° C. for 24 hours.

After the 24 hour incubation, the medium in each culture well is supplemented with HAT selection medium, which selects against the HMS 3.3 parental cell type and all control, nonhybridized splenic mononuclear cells. The cultures are fed aminopterin free HT medium.

After five days in HT medium, the cultures are scored for viability. Conditioned medium is collected from each viable well and immunologically analyzed for the presence of murine immunoglobulins and immunoglobulins reactive to synthetic peptides of angiogenin and to angiogenin itself. Of those cultures producing antibodies immunologically reactive to angiogenin and to peptides of angiogenin, only those cultures of specific antibodies with the highest titers are selected for cloning.

Cloning of the hybridoma cells is accomplished in a manner well known in the art by seeding cells from subcultures to 10×96 well plates, which are plated at a density of 0.3 cells/well. The clones of hybridoma cells are then permitted to grow for ten days while being fed standard cloning medium ad lib.

(b) Purification of Monoclonal Antibodies: The monoclonal antibodies are partially purified from a hybridoma conditioned medium in a multistage process. The medium is clarified initially by filtration, preferably through glass fiber filters. The antibodies in the clarified medium are precipitated by saturated ammonium sulfate, centrifuged to a pellet, decanted, resuspended in saturated ammonium sulfate, recentrifuged to a pellet, resuspended in normal saline (0.15 M NaCl, pH 7.4), and finally dialyzed against normal saline and two changes of distilled water. The resulting partially purified antibody solution is lyophilized and then reconstituted in phosphate buffered saline (pH 7.4).

Alternatively, the monoclonal antibodies in the hybridoma-conditioned medium can be purified to homogeneity by high pressure liquid chromatography after the initial steps of dialysis and washing through a column of Protein A-Sepharose. Fractions of the murine monoclonal antibodies are pooled and then stored at 4° C. for use in the therapeutic and prophylaxis studies described later. Alternatively, the antibodies may be stored for more extended periods of time at −70° C.

C. Efficacy of the Antibodies

Secondary to their ability to react immunologically with angiogenin, the antibodies of this invention possess anti-tumor activity in mammals. In particular, the antibodies of this invention prevented and inhibited tumor growth in mice as determined by immunoprophylactic and immunotherapeutic studies.

Similarly, Fab fragments of antibodies to angiogenin should produce an analogous therapeutic effect since it is well known in the art that the Fab fragments of an antibody possess the antibody binding site and are capable of binding to the antigen as avidly as the intact antibody.

Thus, the immunotherapeutic agents of this invention are monoclonal and polyclonal antibodies and Fab fragments thereof, and mixtures thereof which are immunologically reactive with angiogenin and/or with natural and/or synthetic peptide fragments of angiogenin. These immunotherapeutic agents are useful medicaments in the treatment of pathological processes in mammals where angiogenesis is an undesired manifestation of the process.

Because these immunotherapeutic agents can inhibit angiogenesis, they are particularly useful in the treatment of tumors in mammals.

As pharmaceutical compositions, the immunotherapeutic agents of this invention can be administered in a wide variety of dosage forms, either alone or in combination with other pharmaceutically compatible medicaments, and in the form of pharmaceutical compositions suited for parenteral administration, such as systemic or localized injection, time release implants and the like.

Typically, the immunotherapeutic agents of this invention are administered in the form of pharmaceutical compositions suited for peritoneal administration consisting essentially of the free antibody and a pharmaceutical carrier.

The pharmaceutical carrier can either be a solid or semi-solid material, or a liquid in which the immunotherapeutic agent is dissolved, dispersed, or suspended, and which can optionally contain small amounts of pH buffering agents and/or preservatives. Suitable buffering agents include for example sodium acetate and pharmaceutical phosphate salts and the like. Pharmaceutically acceptable preservatives include for example benzyl alcohol and the like.

Representative of pharmaceutically effective dosage ranges are 8 ng to 200 ng of antibody/dose. However, therapeutically effective dosage ranges can be expected to vary based upon the avidity of the particular antibody selected, the size, age and weight of the patient being treated, and the like, and can readily be determined by simple experiment.

DESCRIPTION OF THE PREFERRED EMBODIMENTS

The following examples are given by way of illustration only and are not to be construed as limiting this invention either in spirit or in scope, as many modifications in materials and methods will be apparent from this disclosure to those skilled in the art.

EXAMPLE 1

Male NZW rabbits weighing 3-5 kg upon arrival were obtained from Millbrook Farms, Mass. and maintained according to AAALAS guidelines.

A breeding colony of Balb/C mice is maintained in The West Quadrangle Animal Facility of Harvard Medical School according to AAALAS guidelines. Mice from this colony are used as thymocyte donors for all hybridization procedures, for all murine immunization procedures, and for approximately 20% of the ascites fluid expansion of selected hybridoma cultures. The colony was originated in 1981 by the crossing of a Balb/CJ female (Jackson Laboratories, Bar Harbor, Me.) with a Balb/CT male (Taconic Farms, Germantown, N.Y.). The F1 pups (8 female and 3 male) were recaged (2-3 females per male) and maintained under aseptic conditions (laminar flow air supply, sterile feed and water), and became the breeding stock for our colony. All mice in this colony have been derived from this original cross and subsequent production of experimental mice has been the result of intra litter, sibling-×sibling mating.

A breeding colony of "nude" mice is housed in the same facility. Mice from this colony are used for all tumor immunotherapy experiments, and for 80% of the in vivo production of monoclonal antibodies by ascites induction. This colony was established in 1982 with the mating of a Balb/CJ (+/+) female to Balb/CT (nu/nu) male. A litter of 4 female and 2 male F1 (+/nu) resulted. Each female was successfully mated with the parental male, resulting in 14 homozygous (nu/nu) nude mice (9 females, 6 males), and 13 heterozygous (+/nu) mice (6 female, 7 male). The 7 male (+/nu) mice were immediately sacrificed, and the remaining mice established into breeding stock (1-2 nu/nu females, 1 +/nu female, and 1 nu/nu male per cage). After 4 generations, (about 6 mo), genetic analysis revealed that the nude gene was in place, and that the offspring ratios were:

nu/nu female:nu/nu male:+/nu female:+/nu male
0.36:0.21:0.25:0.18

These data were consistent with mixed status breeding in which a homozygous nude male is mated with a heterozygous female (0.25:0.25:0.25:0.25) and 1.2 homozygous females (0.5/:/0.5:0:0). It was revealed quickly, however, that homozygous females had other deficiencies (such as limited lactation) which made them relatively poor choices for breeding stock. Although the homozygous females bred 100% nu/nu pups, only about survived through weaning without intervention by "fostering" nu/nu pups to +/nu dames. Consequently, there has been established a system of breeding "tetrads" consisting of 2/+/nu females, 1 nu/nu female, and 1 nu/nu male per cage. At present the breeding colony consists of 21 breeding cages and 19 weanling cages. The present yield of nu/nu mice (surviving through weaning) is approximately 110 female and 90 male per month.

Rabbit Polyclonal Antibody

Preparations of angiogenin were conjugated to an affinity gel, AffiGel 10 (BioRad Laboratories, Burlingame, Calif.), according to manufacturer's instructions, at concentrations of 5 µg (total protein)/ml settled beads. Unreacted sites on the beads were blocked using 1 M ethanolamine and the beads were then extensively washed with coupling buffer, then sterile distilled water. Fifty µl of 10% conjugated bead suspension was emulsified in 1 ml complete (or incomplete) Freund's adjuvant immediately prior to injection.

Alternatively, purified angiogenin and synthetic peptide derivatives were conjugated via glutaraldehyde to keyhole Limpet hemocyanin (KLH) at ratios of 50 µg/mg KLH. The resulting solution was made to 5 mg (total protein)/ml sterile distilled water. Fifty µl (135 µg) KLH-conjugated angiogenin or peptide solution was emulsified in 1 ml complete (or incomplete) Freund's adjuvant immediately prior to injection.

All rabbits were injected subcutaneously at 10 day intervals dorsally, proceeding caudad. Adjuvant was alternated between complete and incomplete Freund's. Sera was collected from rabbits by venipuncture of the marginal ear vein 5 days following each injection, and assayed for the presence of specific antibody by ELISA (enzyme linked immunosorbant assays).

Immunoglobulins were precipitated from sera by the dropwise addition of equal volumes of saturated ammonium sulfate. The resulting suspension was stirred for 1 hr. at room temperature, then centrifuged at 10,000 g. Pelleted material was washed with saturated ammonium sulfate, then resuspended in a minimal volume of 0.15 M NaCl, pH 7.4 (normal saline), loaded into 6000-8000 MW cutoff dialysis tubing, and dialyzed against normal saline. The dialyzed Ig fraction was then applied to a 5 ml bed of Protein A-Sepharose (Pharmacia Fine Chemicals, Piscataway, N.J.), and washed with normal saline. Specifically bound immunoglobulins were eluted from the column in 0.2 M glycine-HCl, pH 3.5. These fractions were neutralized by immediate collection into 0.1 volume of 1 M Tris Cl, pH 8.0, pooled, and dialyzed as above. The dialyzed material was applied to a 20 ml bed of DEAE-cellulose and the leading fractions (unbound) were collected, pooled, dialyzed against distilled water, then lyophilized.

EXAMPLE 2

Mouse Monoclonal Antibody

Five µg of purified angiogenin was conjugated to an immunization matrix consisting of $5 \times 10^9$ submicro beads, Covaspheres-MX (Covalent Technologies, Inc., Ann Arbor, Mich.), according to manufacturer's instructions. Unreacted sites on the beads were blocked by incubation with autologous mouse serum, and the beads were washed extensively then resuspended in 1 ml 20 mM sodium phosphate buffer (pH 7.4). The conjugated bead suspension was sonicated briefly and the 50 µl of the bead "slurry" was emulsified in complete Freund's adjuvant immediately prior to injection.

Balb/C mice were immunized by intraperitoneal injection of conjugated beads in complete Freund's adjuvant at 10 day intervals for 90 days. Sera was collected by venipuncture of the tail vein 5 days following each injection, and assayed for the presence of specific antibody by ELISA. Four days prior to hybridization, mice were injected intravenously with 50 ng purified angiogenin.

Fusion 38 was a somatic cell hybridization between the splenic lymphocytes of an immunized Balb/C mouse and plasmacytoma cells from a subline of P3×63Ag8.653 (CRL 1580) designated as HMS 3.3.

The antigen used in the immunization procedures was human angiogenin, purified to homogeneity from medium conditioned by the colonic adenocarcinoma cell line HT-29, and conjugated to a submicro bead immunization matrix, Covaspheres-MX (Covalent Technologies Corp., Ann Arbor, Mich.), at levels of 1 ng/$5 \times 10^9$ beads. The mouse was injected intraperitoneally at 10 day intervals with $5 \times 10^7$ antigen-conjugated beds suspended in 1 ml Complete Freunds' adjuvant. Serum samples were collected twice monthly, and assayed for specific binding to any of 3 synthetic polypeptides derived from the sequence of native angiogenin. Upon detection of circulating antibody reactive with any of the peptides, the mouse was injected intraperitoneally with a $2 \times$ dose of antigen conjugated beds suspended in sterile saline.

Four days following the injection, the mouse was sacrificed and the spleen harvested. After mechanical disruption of the spleen by passage through a 500 μm stainless steel mesh, the mononuclear cells were purified by density gradient centrifugation. The splenic lymphocytes thus obtained were mixed (1:1) with $1 \times 10^8$ HMS 3.3 cells and pelleted by centrifugation (supernatant discarded). The co-pelleted cells were fused by the slow addition of polyethylene glycol (400–600/cp) to 50% (v/v), then washed free of the PEG by centrifugation. The resulting cell pellet was resuspended in RPMI-1640 medium supplemented with 10% fetal bovine serum, anti-microbial agents and 50% thymocyte-conditioned RPMI-1640. The resuspended cells were plated to $10 \times 96$ well tissue culture plates (100 μl/well) and incubated at 37° C. for 24 hrs.

After 24 hrs. incubation, the medium in each well was supplemented with HAT selection medium which selects against the HMS 3.3 parental cell type. The cultures were refed ad lib with HAT selection medium until day 21 post fusion, when they were fed aminopterin-free Ht medium. By this time, all control, nonhybridized splenic mononuclear cultures were non-viable. After 5 days in HT medium, the plated cultures were scored for viability, conditioned medium was collected from each viable well for immunological analysis. Conditioned medium samples were assayed by ELISA procedures for the presence of murine immunoglobulins and for specific antibodies reactive with the synthetic peptides STP-7, STP-8, and STP-12.

Results: Ten fusions utilizing the above protocols were performed. Viable heterokaryons were detected in 6326 of 8000 subcultures plated. Secreted immunoglobulin concentrations of $>1$ μg/ml were detected in 2111 of 6326 viable cultures. Seven of 2111 cultures contained detectable quantities of antibody specific for one or more of the synthetic peptides (STP-7, −8, or −12) and for native angiogenin.

Larger quantities of specific antibodies or higher titered antibodies were detected in subcultures F38-05 and F38-10, and these were selected as primary candidates for cloning procedures. Cells from each subculture were seeded to $10 \times 96$ well tissue culture plates which were plated at a density of 0.3 cells/well, and allowed to grow for 10 days while being fed standard cloning medium ad lib.

Sixteen non-identical clones with specificity toward peptides or native angiogenin were identified from subculture F38-05. All were characterized as IgG1,k, with pI's ranging from 8.2 to 8.8. Of these clones, only F38-05.008 was capable of secreting $>1$ μg antibody/$1 \times 10^6$ cells/24 hr., and this clone was selected for expansion to larger scale in vitro production.

Immediately following cloning procedures, selected cells were expanded into 2 cm² TC vessels in the presence of standard LY-10 lymphocyte growth medium (RPMI 1640 containing 10% fetal bovine serum, 2 mM L-glutamine, antimicrobials and 1/mM sodium pyruvate). At densities of $5 \times 10^5$ cells/ml, the cultures were at first expanded to 75 cm² vessels and then to 150 cm² vessels. At this point, cells were multiply cyropreserved in 5–10 vials containing $1-5 \times 10^6$ cells/ml of fetal bovine serum containing 10% DMSO.

Intermediate to large-scale cultures ($1-5 \times 150$ cm² flasks, then $1-2 \times 6000$ cm² "cell factories") were established for each clone at densities approaching $5 \times 10^5$ cells/ml. At weekly intervals, conditioned medium was collected from the growth vessels. The "cell factories" were reseeded with $1-2 \times 10^7$ cells in 2 L fresh LY/10 medium, and returned to incubation. The conditioned medium was clarified by filtration through Whatman glass fiber filters, then concentrated 50–80 fold by ultrafiltration in an Amicon DC-2 filtration device fitted with dual 20,000 MW cutoff hollow fiber filters. The retained medium was then stored at −20° C. for further purification. At monthly intervals, cyropreserved cells from each clone were returned to culture, and upon attainment of appropriate cell densities, were placed into large scale culture, replacing the "current" production lots.

Partial purification: Hybridoma-conditioned medium was clarified by filtration through Whatman glass fiber filters. Equal volumes of saturated ammonium sulfate were added dropwise to the clarified hybridoma-conditioned medium and stirred for 1 hr at room temperature. The mixture was centrifuged (10,000 g) for 10 minutes and the resulting pellet resuspended in saturated ammonium sulfate and washed by centrifugation. Pelleted material was resuspended in normal saline and dialyzed as above against normal saline and two changes of distilled water. The antibody solution was then lyophilized, and reconstituted in phosphate buffered saline, pH 7.4.

Purification to homogeneity: Clarified hybridoma-conditioned medium was dialyzed overnight at 4° C. in 6000–8000 MW cutoff bags against 50 volumes 0.1 M sodium phosphate buffer, pH 8.0. This material was applied to a 5 ml bed of Protein A-Sepharose. Unbound material was washed from the column using 0.1 M sodium phosphate buffer, pH 8.0, and Ig enriched fraction also from the column in 0.1 M sodium citrate buffer, pH 3.5. This immunoglobulin-enriched fraction was neutralized by collection into 1 M Tris buffer, pH 8.0, then dialyzed against distilled water, and lyophilized. The lyophilized fraction was reconstituted in 20 mM Tris-HCl, pH 8.5, dialyzed overnight against the same buffer, and clarified by centrifugation through 0.8 μm pore size cellulose acetate microfilter (Schliecher and Schuell). The solution was injected onto a Mono Q HR5/5 Pharmacia high performance liquid chromatography column, equilibrated with 20 mM Tris-HCl, pH/8.5. After washing in the above buffer for 5 minutes (0.8/ml/min), a linear gradient from 0 to 0.5 M NcCl and pH 8.5 to 7.0 was applied to the column over a period of 50 minutes (Buffer 1=20 mM Tris-HCl, pH 8.5; Buffer 2=20 mM Tris HCl+0.5 M NaCl, pH 7.0). Resulting fractions were analyzed for murine and bovine IgG by standard ELISA (enzyme linked immunosorbant assay) procedures. Fractions containing murine but not bovine IgG were pooled and stored at 4° C. (or 70° C.) for later use.

EXAMPLE 3

Immunotherapeutic Protocol

In these studies, male nu/nu Balb/C mice (7-9 weeks) were cage- and weight matched (5/cage) as closely as possible. Experimental groups of 5-10 mice were randomized by cages prior to experimentation.

The experimental mice were challenged with $5-10 \times 10^5$ HT-29 cells on day zero. Antibody administration by intraperitoneal injection was begun only after tumor masses were detectable by palpation in all experimental animals. Five to ten antibody doses were administered at 2-3 day intervals thereafter, with assessments of general health, body weight, tumor mass sizes, and photographic records taken 2-3 times/week.

A control group of more than 900 mice was challenged with $5 \times 10^5$ HT-29 tumor cells and given "sham" treatments consisting of any of the following: physiological saline, non immune mouse or rabbit immunoglobulins, or irrelevant monoclonal immunoglobulin derived from the plasmacytoma cell line, MOPC 21.

In the test group of mice receiving doses of polyclonal antisera to angiogenin (1 mg/dose immunoglobulin enriched fractions of rabbit antisera made against relatively crude angiogenin preparations), tumors regressed to approximately 30% of mass size, whereas, the tumor mass in the control group increased steadily. After cessation of immunotherapy, the mass size of tumors in the test groups increased steadily at approximately the mean rate of the tumors in the control groups. Occasionally, 5-10% of the time, tumors in the test group would regress to the point of non-detectability. Upon the cessation of treatment, these nondetectable tumors continued to remain nondetectable both throughout the course of the experiment and upon histological examination of the animal at the conclusion of the experiment.

In the control group, tumor masses developed in 100% of the challenged mice with no spontaneous size regression.

The immunotherapy studies on the murine antiangiogenin monoclonal antibodies were scored as discrete binomial events at the end of the experimental period (21-35 days), wherein the presence of any detectable tumor was scored as a negative result and only the complete abolition of the prior existing tumor mass was scored as a positive result.

The results are tabulated in Table 1, in which $$\text{"Cure" rate} = \frac{\text{number of "positive" results}}{\text{total number of "surviving" mice}}$$

TABLE 1

| Monoclonal Antibody Prep Number | Antibody Dose (ng) | Positive/Surviving | "Cure Rate" % |
|---|---|---|---|
| F38-0.5.008p1 | 200 | 14/43 | 32.6 |
| | 40 | 25/85 | 29.4 |
| | 8 | 12/35 | 34.3 |
| F38-05.008p2 | 200 | 4/28 | 14.3 |
| | 40 | 6/39 | 15.4 |
| | 8 | 7/27 | 25.9 |
| F38-05.008p3 | 200 | 0/16 | 0.0 |
| | 40 | 0/13 | 0.0 |
| | 8 | 3/18 | 42.6 |
| Combined | 200 | 18/87 | 20.7 |
| | 40 | 31/137 | 22.6 |
| | 8 | 22/80 | 27.5 |

The combined data from Table 1 summarize the results of nine different experiments conducted on three different preparations of the murine monoclonal antibody F38-05.008 to human tumor angiogenin. The results indicate that the monoclonal antibody to human tumor angiogenin was able to exert an immunotherapeutic effect on solid tumors from the colonic adenocarcinoma cell line HT-29 to the extent that total abolition of an existing tumor mass occurred in 20.7 to 27.5% of the cases. A "cure rate" of 0.0 was obtained utilizing any of the "sham" treatments listed above. The monoclonal antibody to human tumor angiogenin should effect a similar cure rate on other solid tumors since the growth of other solid tumors is also dependent upon an extensive vascular network which is produced as a result of angiogenin stimulation.

The data from Table 1 further indicate that although an optimal dosage of antibody has not been obtained, higher cure rates are obtained with lower doses of antibody (8 ng. v. 200 ng.). Optimal dosage can be determined by simple experimentation.

EXAMPLE 4

Generation of Antibodies to Angiogenin Using Peptide Fragments

Synthetic polypeptides were prepared corresponding to the amino acid sequences of each of the following sequences of Formula I: 6-21, 108-121, and 15-26. In each case, the polypeptide corresponding to the specified fragment of angiogenin was prepared by solid phase Merrifield synthesis on a polymer bead, then liberated with hydrofluoric acid and purified by high performance liquid chromatography, procedures which are all well known. See Barany and Merrifield, Peptides, Vol. 2, Special Methods in Peptide Synthesis, Part A, p. 3, Ed. Gross and Meinhofer, Academic Press N.Y. (1980) and Merrifield, Adv. Enzymology, Vol. 33, 221-296 (1969).

Each such synthetic peptide fragment was coupled to keyhole limpet hemocyanin (KLH) with glutaraldehyde by conventional procedures, and the products were dialyzed against physiological saline.

The dialyzed products were used to immunize rabbits monthly subcutaneously with 100 μg peptide equivalents of the peptide/KLH mixtures employing, alternately, complete and incomplete Freund's adjuvant according to standard protocols. Blood samples were drawn monthly.

From each blood sample IgG was isolated from the immune serum by ammonium sulfate precipitation, Protein A—Sepharose chromatography, and DEAE ion-exchange chromatography to provide purified antibody.

Immunoreactivity of each antibody toward the peptide fragment and toward native whole angiogenin was assessed by enzyme-linked immunosorbent assay (ELISA). It was found that all three were immunoreactive to whole angiogenin. Other synthetic peptides have been prepared corresponding to fragments 30-41, 36–46, 48–61, and 108–123 of Formula I and are being assayed.

What is claimed is:

1. A pharmaceutical composition comprising a therapeutically effective amount of an antibody immunologically reactive to angiogenin having the amino acid sequence of 1
<Glu—Asp—Asn—Ser—Arg—Tyr—Thr—His—Phe—Leu—

15
—Thr—Glu—His—Tyr—Asp—Ala—Lys—Pro—Gln—Gly—

30
—Arg—Asp—Asp—Arg—Tyr—Cys—Glu—Ser—Ile—Met—

—Arg—Arg—Arg—Gly—Leu—Thr—Ser—Pro—Cys—Lys—

45
—Asp—Ile—Asn—Thr—Phe—Ile—His—Gly—Asn—Lys—

60
—Arg—Ser—Ile—Lys—Ala—Ile—Cys—Glu—Asn—Lys—

—Asn—Gly—Asn—Pro—His—Arg—Glu—Asn—Leu—Arg—

75
—Ile—Ser—Lys—Ser—Ser—Phe—Gln—Val—Thr—Thr—

90
—Cys—Lys—Leu—His—Gly—Gly—Ser—Pro—Trp—Pro—

—Pro—Cys—Gln—Tyr—Arg—Ala—Thr—Ala—Gly—Phe—

105
—Arg—Asn—Val—Val—Val—Ala—Cys—Glu—Asn—Gly—

120
—Leu—Pro—Val—His—Leu—Asp—Gln—Ser—Ile—Phe—

123
—Arg—Arg—Pro—OH in a pharmaceutical carrier.

* * * * *